United States Patent [19]
Clark et al.

[11] Patent Number: 5,970,438
[45] Date of Patent: Oct. 19, 1999

[54] METHOD AND APPARATUS FOR TESTING RAILS FOR STRUCTURAL DEFECTS

[75] Inventors: Robin Clark; Jeff Boyle, both of Fairfield, Conn.; Spencer Morgan, Hamilton, Ohio; Alastair Veitch, Fairfield, Conn.

[73] Assignee: Sperry Rail Service, Danbury, Conn.

[21] Appl. No.: 09/056,829

[22] Filed: Apr. 7, 1998

[51] Int. Cl.[6] .......................... G01M 19/00; G01N 29/04
[52] U.S. Cl. .............................. 702/184; 702/35; 702/33; 73/636; 73/146
[58] Field of Search ................................ 702/184, 35, 33, 702/103, 171; 73/636, 634, 633, 635, DIG. 6, 146; 324/217; 340/870.16

[56] References Cited

U.S. PATENT DOCUMENTS

| | | | |
|---|---|---|---|
| 3,718,040 | 2/1973 | Freman et al. | 73/146 |
| 3,924,461 | 12/1975 | Stover | 73/146 |
| 4,468,966 | 9/1984 | Bradshaw | 73/636 |
| 4,578,665 | 3/1986 | Yang | 702/188 |
| 4,689,995 | 9/1987 | Turbe | 73/636 |
| 5,574,224 | 11/1996 | Jaeggi | 73/636 |
| 5,627,508 | 5/1997 | Cooper et al. | 73/636 |

*Primary Examiner*—Louis Arana
*Assistant Examiner*—Hien Vo
*Attorney, Agent, or Firm*—J. Michael Martinez de Andino; McGuire, Woods, Battle & Boothe LLP

[57] ABSTRACT

A method and apparatus for testing rails for structural defects, the rails being associated with a railroad track include providing and using a first rail traveling vehicle for movement along a segment of rails followed by a second rail traveling vehicle for disposition behind the first rail traveling vehicle along the rails for testing with the first rail traveling vehicle having a first digital computer and a first analog computer and the second rail traveling vehicle having a second computer for display of data associated with the rails. A first modem assembly is provided in the first vehicle with a second modem assembly being provided in the second vehicle in communication with the first modem whereby data may be exchanged between the rail traveling vehicles. During testing, the first rail traveling vehicle transmits complete digital and analog rail structural and defect location information data to the second computer for analysis and action by the operators of the second vehicle.

29 Claims, 6 Drawing Sheets

| Supects: 8 | | Waiting for: na | | | Requests: na | | | |
|---|---|---|---|---|---|---|---|---|
| 0.0000 | Segment | Record | Y | Type | ROp | Eop | Mileage | ExamOp: JLR |
| 1 | 1024-6143 | 1722 | 74 | NHT | BJL | JLR | 0.0070 | |
| 2 | 1024-6143 | 3254 | 79 | NHT | BJL | JLR | 0.0822 | |
| 3 | 1024-6143 | 4555 | 82 | NHT | BJL | JLR | 0.1459 | |
| 4 | 19456-20479 | 20167 | 57 | 1007 | BJL | JLR | 0.9088 | |
| 5 | 22528-23551 | 22773 | 85 | 1008 | BJL | JLR | 1.0363 | |
| 6 | 55296-56319 | 55783 | 79 | ALARM | BJL | | 2.6540 | |
| 7 | 58368-60415 | 59328 | 61 | NHT | BJL | JLR | 2.8282 | |
| 8 | 62464-63487 | 63195 | 78 | EBF | BJL | | 3.0183 | |

METHOD AND APPARATUS FOR TESTING RAILS FOR STRUCTURAL DEFECTS

BACKGROUND OF THE INVENTION

The present invention relates broadly to apparatus and methods for testing rails, especially rails laid along a roadbed to form a railroad track. More particularly, the present invention is directed to a method and apparatus for testing rails using two linearly disposed rail-traveling vehicles and radio-based voice and data communication for data transfer therebetween to include the transfer of rail defect data acquired by the lead vehicle to the trailing vehicle.

Steel rails, such as those used for railroad tracks which extend in a linear, generally parallel relationship, can develop internal structural defects such as stress fractures and other metallic structural anomalies. Such defects, if left unattended, can cause failure, especially fatigue failure, due to the repetitious loading and unloading of the rails by passing trains. Such rail failures can result in disrupted schedules as well as train derailments.

As a response, it is generally known to periodically test the rails using some form of test system. The common form of rail testing involves ultrasonic technology. Specialized rail traveling vehicles carry ultrasonic transducers which transmit sound into the rails and receive and analyze return echo signals. Certain disruptions in the signal may be interpreted as rail defects and certain types of defects will reflect a characteristic signal such that when the characteristic signal is received, the type of defect may be readily determined. Typically, the transducers are carried on wheels or carriages, which are mounted on rail traveling vehicles such that the wheels are maintained in rail contact. Further, the transducers typically propagate waves at 0°, 37° and 70° into the rails. The rail traveling vehicles also carry computers which can receive signals from the transducers, process the signals and interpret signal anomalies as defects and can also locate the defect within the rail. General ultrasonic inspection theory may be reviewed with reference to Norris, U.S. Pat. No. 4,429,576; Pagano et al., U.S. Pat. No. 4,487,071; or Cowan, U.S. Pat. No. 3,415,110. All three patents are referenced for their general teachings regarding ultrasonic rail testing.

Typically, a rail traveling vehicle will carry the transducer system including a computer for data analysis. The vehicle will also typically carry an encoder which includes another rail contact wheel having a signal generating device associated therewith for periodic signals which are related to distance traveled from a predetermined starting point such that the location of the test vehicle may be determined by its displacement from a reference position.

Federal Railroad Administration (FRA) rules provide that if the test vehicle identifies a suspicious location on the track, then the vehicle must stop and personnel must confirm the presence or absence of a defect at that location. Utilizing a single vehicle, the test vehicle would be continually moving down the track, stopping, then reversing to investigate indications identified by the test equipment. The speed at which this can be accomplished limits the amount of track that can be tested in a single day or other predetermined time period. In order to increase the amount of track tested per day, the chase car, or two vehicle system, has been developed. This system employs an additional vehicle, i.e., a second or chase vehicle that follows the test vehicle along the track. The chase vehicle is typically a smaller vehicle than the test vehicle with a minimum amount of equipment carried therein. The test vehicle is configured with a rail inspection system and the chase vehicle is configured for receipt of communication from the test vehicle and is sufficiently equipped to allow personnel to conduct the necessary confirmation.

Currently, data sent from the test vehicle to the chase vehicle is minimalistic and typically involves a form of code to indicate that a defect has been found and a printer which will receive data from the test vehicle indicating where the defect was found. Personnel on the chase car must then use their own test equipment to verify the defect. The problem with this approach is that many of the test vehicle capabilities are not fully realized because the data sent to the chase vehicle is minimal and tests performed by the test vehicle must be reperformed by personnel from the chase vehicle.

SUMMARY OF THE INVENTION

It is, accordingly, an object of the present invention to provide a method and apparatus for testing rails for structural defects which includes transferring data to the chase vehicle which allows personnel within the chase vehicle to confirm a defect identified by the test vehicle within reduced time and effort over the prior art.

It is further an object of the present invention to provide such a method and apparatus which will allow rapid and complete confirmation of all data gathered by the test vehicle to provide a complete record of rail test data.

To that end, a method for testing rails for structural defects, with the rails being associated with a railroad track, ground supported and extending in a generally parallel manner along a road bed includes the steps of providing a first rail traveling vehicle for movement along a segment of rails for testing, the first rail traveling vehicle being equipped with a rail testing apparatus for production of data indicative of rail conditions and a first computer system in data exchanging communication with the rail testing apparatus, the first computer system having a display arrangement for displaying digital data and analog data associated with rails tested by the rail testing apparatus and a control interface for computer control by an operator; providing a second rail traveling vehicle for disposition behind the first rail traveling vehicle along the segment of rails for testing, the second rail traveling vehicle having a second computer disposed therein for display of data associated with rails tested by the rail testing apparatus; providing a first modem assembly operatively associated with the first computer and a second modem assembly operatively associated with the second computer with the first modem assembly being in data exchanging communication with the second modem assembly for data exchange between the first computer and the second computer.

The method further includes the steps of moving the first rail traveling vehicle and second rail traveling vehicle along rails to be tested with the first rail traveling vehicle moving in advance of the second rail traveling vehicle; testing predetermined rail segments using the rail testing apparatus with the rail testing apparatus communicating rail test data associated with the structural condition of a tested rail segment to the first computer; displaying the rail test data on a computer screen wherein the rail test data may include data indicative of a structural defect in the predetermined rail segment at a defect location along the rail. The method further includes the steps of assessing the rail test data to determine if the rail test data is indicative of a possible structural defect in the predetermined rail segment at a defect location; selecting, upon determination of a possible structural defect, data indicative of the possible structural defect at the defect location, thereby creating a data snapshot of structural conditions along the segment of rails having the possible defect therein; communicating the data indicative of the possible structural defect at the defect location from the first computer system to the second computer using the first modem assembly and the second modem assembly; displaying the data indicative of the possible structural defect at the defect location using the second computer and assessing the data indicative of the possible structural defect at the defect location to locate the defect location and the possible structural defect in order to carry out a manual defect confirmation test and, if necessary, to initiate repair procedures.

Preferably, the step of providing a first computer system includes providing a first digital computer and further includes providing a first analog computer in data exchanging communication with the first digital computer, with the first digital computer being for processing digital rail test data and the first analog computer being for processing analog rail test data. It is further preferred that the step of providing a first computer system includes providing a first display arrangement associated with the first digital computer for displaying digital rail test data and a second display arrangement associated with the first analog computer for displaying analog rail test data and the step of assessing the rail test data includes viewing and assessing digital rail test data in conjunction with corresponding analog rail test data to determine if the rail test data is indicative of a possible structural defect in the predetermined rail segment at a defect location.

Preferably, the step of communicating data indicative of the possible structural defect to the second computer includes communicating digital rail test data and possible defect location data to the second computer. It is further preferred that the step of communicating data indicative of the possible structural defect to the second computer includes communicating the analog rail test data to the second computer.

It is preferred that the step of selecting data indicative of a possible structural defect, thereby creating a digital snapshot of structural conditions, include the first digital computer communicating with the first analog computer to capture analog data selected, the analog data selected being indicative of a defect and a location of the defect. Preferably, the step of providing the first computer system includes providing a light pen used to select data by touching the light pen to a display and the step of selecting data indicative of a possible structural defect, thereby creating a data snapshot of structural conditions includes using the light pen to select data by touching the light pen to the digital display and a position on the display corresponding to a possible defect location. It is further preferred that the step of selecting data indicative of a possible structural defect, thereby creating a digital snapshot of structural conditions includes creating a snapshot of data corresponding to a rail segment having a linear dimension in the range of approximately 80–120 feet. Further, the step of selecting, upon detection of a possible structural defect, data indicative of the possible structural defect at the defect location includes the step of selecting a defect classification from a list of predetermined defect classifications stored in the first computer. Additionally, the step of selecting data indicative of the possible structural defect at the defect location includes the step of confirming the selection of a defect prior to communicating the rail test data to the second computer and, if the confirmation step is omitted, test data conforming to a predetermined rail length is transmitted automatically. If the confirmation is retracted no data is transmitted. The method further, preferably, includes the step of applying paint to the rails in a predetermined manner based on particular combinations of test data.

Preferably, the step of providing a first modem assembly operatively associated with the first computer and a second modem assembly operatively associated with the second computer with the first modem assembly being in data exchanging communication with the second modem assembly for data exchange between the first computer system and the second computer includes the step of providing a first radio transmitter and receiver operatively associated with the first computer system and a second radio transmitter and receiver operatively associated with the second computer for maintaining radio communication between the first computer and the second computer for wireless data exchange there between. Preferably, the step of providing radio transmitters and receivers includes providing an arrangement for determining when communication between the first computer and the second computer have been terminated operatively associated with the first computer and the second computer and upon discovery of such termination of communications, the method further includes the step of alerting operators to such termination and the step of resending all data that has not been acknowledged by the second computer.

It is further preferred that the step of providing a second display includes providing the second display with information regarding a location of the first traveling rail vehicle along the rails and upon loss of location information, the method includes the step of determining that the communication has terminated. The method further, preferably, includes the step entering results associated with the manual rail test into the second computer and communicating the result data to the first computer.

An apparatus for testing rails for structural defects, the rails being associated with the railroad track, ground supported and extending in a generally parallel manner along a road bed includes a first rail traveling vehicle for movement along a segment of rails for testing, the first rail traveling vehicle having a real testing apparatus for the production of data indicative of rail conditions mounted thereto; a first computer system mounted within the first rail traveling vehicle in data exchanging communication with the rail testing apparatus, the first computer having a display arrangement for displaying digital data and analog data associated with rails tested by the rail testing apparatus; and a control interface for computer control by an operator; a second rail traveling vehicle for disposition behind the first rail traveling vehicle along the segment of rails for testing; a second computer disposed in the second rail traveling vehicle for display of data associated with rails tested by the rail testing apparatus; a first modem assembly operatively associated with the first computer and mounted within the first rail traveling vehicle; a second modem assembly operatively associated with the second computer and disposed within the second rail traveling vehicle, the first modem assembly being in data exchanging communication with the second modem assembly for data exchange between the first computer and the second computer to communicate data indicative of a possible structural defect at a defect location to the second computer using the first modem assembly and the second modem assembly; and an arrangement for displaying data indicative of the possible structural defect at the defect location operatively associated with the second computer for assessment of the data indicative of the possible structural defect at the defect location to locate the defect location and the possible structural defect in order to carry out a manual defect confirmation test and, if necessary, to initiate repair procedures.

The first computer system preferably includes a first digital computer and further preferably includes a first analog computer in data exchanging communication with the first digital computer with the first digital computer including an arrangement for processing digital rail test data and the first analog computer includes an arrangement for processing analog rail test data. The first computer system preferably includes a first display apparatus operatively associated with the first digital computer for displaying digital rail test data and a second display apparatus operatively associated with the first analog computer for displaying analog rail test data for assessment of the rail test data by action of an operator in viewing and assessing digital rail test data in conjunction with corresponding analog rail test data to determine if the rail test data is indicative of a possible structural defect in the predetermined rail segment at a defect location. The first computer system preferably includes an arrangement for communicating the data indicative of the possible structural defect including analog rail test data to the second computer. Preferably, the first digital computer includes an arrangement for communicating with the first analog computer to capture analog data selected by an operator, the analog data being indicative of a defect and a location of the defect.

Preferably, the control interface includes a light pen for use by an operator to select data by touching the light pen to a position on the display corresponding to a possible defect location with the data being indicative of a possible structural defect to thereby create a digital snapshot of structural conditions. Preferably, the apparatus for testing rails includes an arrangement for applying paint to the rails in a predetermined manner based on particular combinations of test data. Additional paint may be laid down every 0.1 miles for aiding and determining the location on the track.

The apparatus further preferably includes a first radio transmitter and receiver operatively associated with the first modem assembly and a second radio transmitter and receiver operatively associated with the second modem assembly for maintaining radio communication between the first computer and the second computer for wireless data exchange there between. The apparatus further preferably includes an arrangement for determining when communication between the first rail traveling and the second rail traveling vehicle have been terminated and an arrangement for, upon discovery of such termination of communications, alerting operators to such termination, operatively associated with the transmitters and receivers.

By the above, the present invention provides a method and apparatus for testing railroad track rails for structural defects which provides enhanced efficiency with respect to the use of time and equipment.

BRIEF DESCRIPTION OF THE DRAWINGS

FIG. 6 is a depiction of a screen display illustrative of the second computer according to the preferred embodiment of the present invention.

DESCRIPTION OF THE PREFERRED EMBODIMENT

Figure 1:
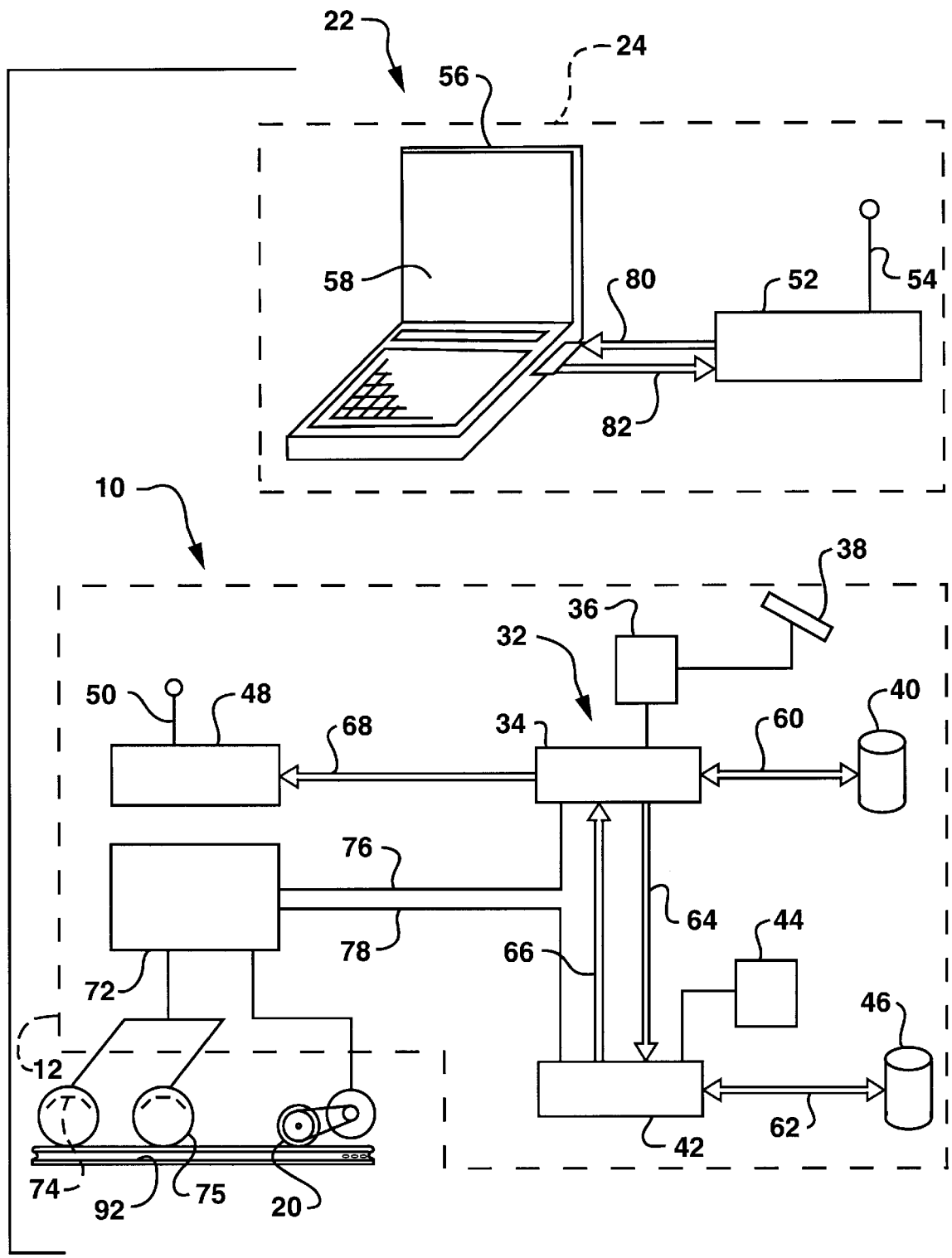
FIG. 1 is a diagrammatic view of an apparatus for testing rails for structural defects according to the preferred embodiment of the present invention.
Figure 3:
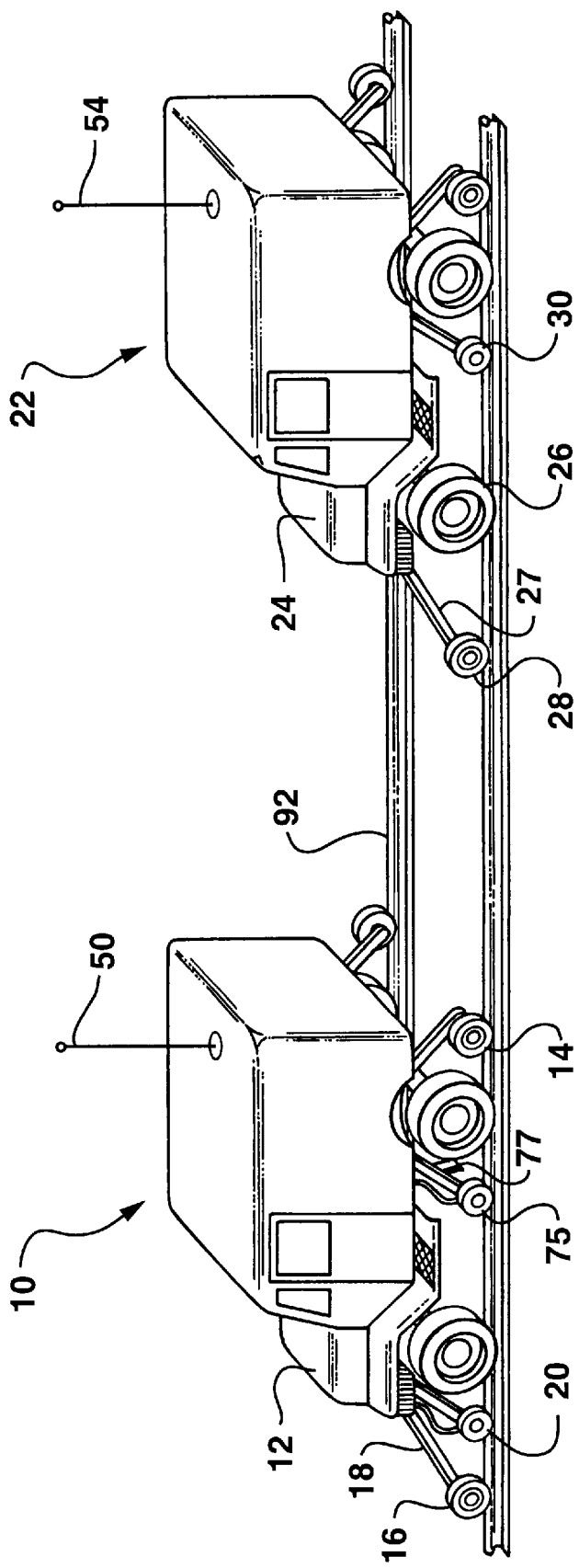
FIG. 3 is a prospective view of a two-car rail testing system according to the preferred embodiment of the present invention.

Turning now to the drawings, and more particularly to FIG. 1, an apparatus for testing rails for structural defects according to the preferred embodiment of the present invention is illustrated. FIG. 1 illustrates a first test vehicle 10 and a second, chase vehicle 22, in a very basic, outline form. As seen in FIG. 3, the test vehicle 10 is disposed on parallelly extending, ground supported rails 92 for testing while the chase vehicle 22 is disposed behind the test vehicle 10. The test vehicle 10, disposed in advance of the test vehicle 10, includes a body 12 which houses a driver, operator and other equipment and personnel as will be seen in greater detail hereinafter. The chase vehicle 22 is supported for rail traveling movement by rail support wheels 16 which extend outwardly from wheel support members 18. The wheel support members 18 project outwardly from four corners of the test vehicle 10 to support the wheels 16, and, consequently, the vehicle 10 for rail contacting movement. The rail traveling vehicle 10 also includes pneumatic tires 14, which can allow the first rail traveling vehicle 10 to move when not disposed on the rails 92.

The second or chase vehicle 22 also includes a body 24 and rail contacting wheels 28 supported by support members 27 projecting outwardly from four corners of the vehicle body 24. The first and second rail traveling vehicles 10, 22 each include an antenna 50, 54 respectively for communication therebetween. It will be appreciated by those skilled in the art that the rail traveling vehicles 10, 22 depicted herein are depicted for illustrative purposes only and that the actual configuration of vehicles used may vary from that shown in the diagrams.

Returning now to FIG. 1, the first rail traveling vehicle is illustrated generally at 10 with the body containment boundary illustrated at 12. The test vehicle 10 includes an ultrasonic rail testing apparatus 72 which will be explained in greater detail presently. The rail testing apparatus 72 is operatively connected to roller search units 75 which carry a plurality of transducers 74. The roller search units 75 roll along in a rail contacting manner to periodically present the transducers to the rails so that the transducers may send and receive high amplitude, short pulsed, sound waves to and from the rails at predetermined angles of incidence and refraction. Rails with defects return signals earlier at the deflection location than those without defects. Typically, the waves are propagated at 0°, 37° and 70° into the rails. A distance measuring encoder 20 is also incorporated into the test vehicle 10. The encoder sends periodic signals to determine the distance traveled by the test vehicle from a reference point. Signals are outputted from the transducer 74 and the encoder 20 and are fed to the ultrasonic test apparatus 72.

Figure 2:
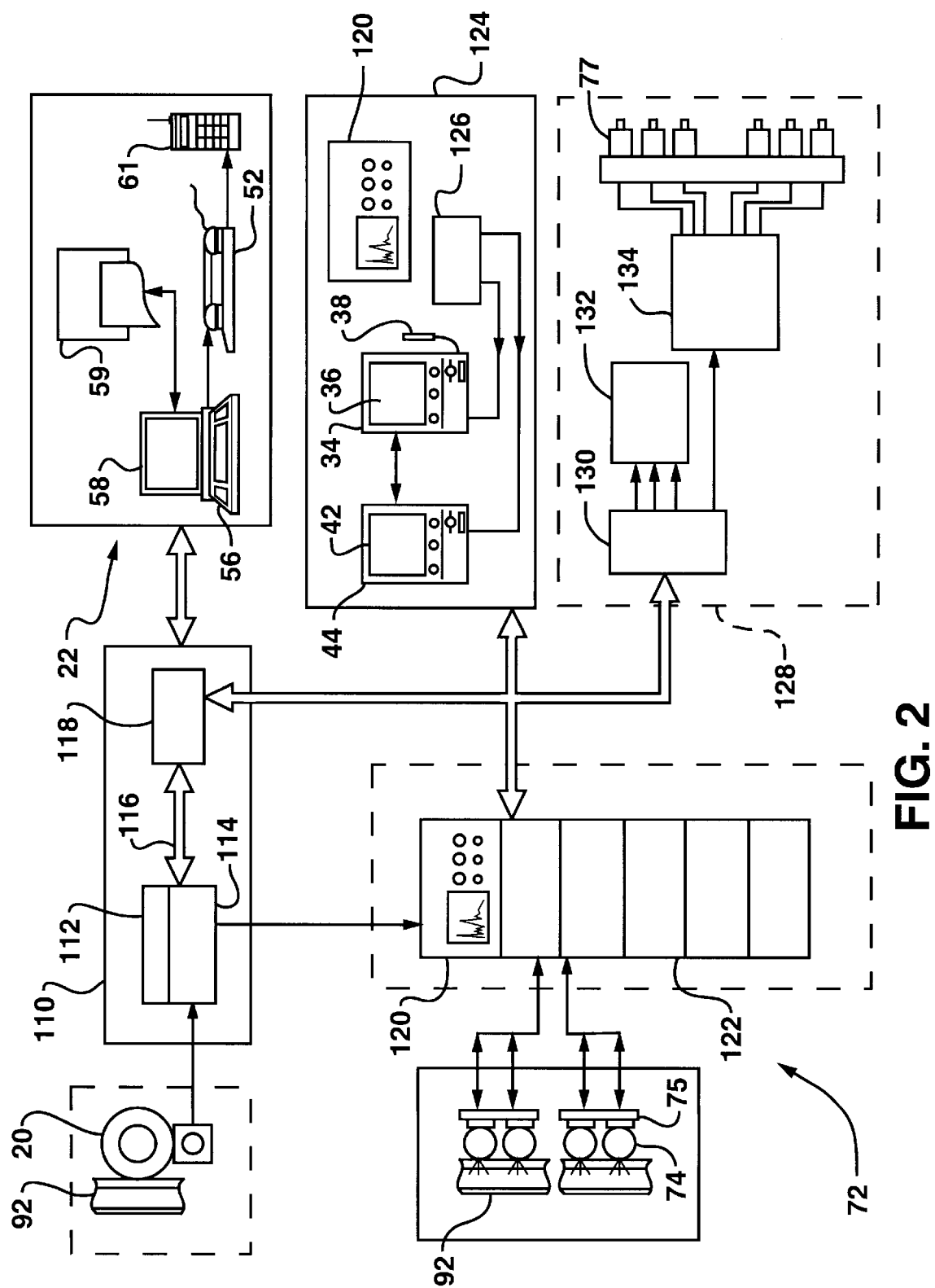
FIG. 2 is a diagrammatic view of portions of the system illustrated in FIG. 1, providing a more detailed view of the rail testing apparatus.

Turning now to FIG. 2, the ultrasonic rail test apparatus 72 includes an ultrasonic signal processor 122 which includes gating and level detection as well as real time defect detection logic and real time computer integration circuitry and a monitor scope 120. The monitor scope 120 can provide instantaneous representations of the ultrasonic signals traveling within the rails 92.

The encoder 20 sends its output to a milepost monitor 110 which includes a reference point determinator 112 and a driver milepost monitor circuit 114 which sends an output signal to the monitor scope 120. An operator milepost monitor circuit 118 is in communication with the driver milepost monitor circuit 112 through a milepost monitor link 116. A defect/alarm monitoring system 128 is also included and the alarm/marking system 128 includes an alarm/paint gun interface 130 which provides signal output to audiovisual alarms 132 and to a paint gun driver 134 which controls paint guns 77 as seen in FIGS. 2 and 3 which will apply paint to the track at a particular configuration for particular test data at a particular or predetermined location. The defect/alarm monitor is in two-way communication with the operator milepost monitor to provide distance, displacement or location calibration information to the marking system. The ultrasonic signal processor 122 is in two-way communication with an operator console 124 which includes a second monitor scope 120. The second monitor scope 120 is associated with the ultrasonic signal processing system 122 yet resides in the operator console 124.

The operator console 124 also includes a digital computer 34 having a digital display 36 and an analog computer 42 having an analog display 44. Both are supplied with power from an uninterruptable power source 126. A light pen 38 is attached to the digital computer 34 to act as an operator controlled interface for selecting items on the display 36. While the previous discussion of items depicted in FIG. 2 includes items found in the test vehicle, FIG. 2 also illustrates items found in the chase vehicle 22 as depicted therein. There, a second computer 56 including a second display 58 is provided along with a printer 59, a radio modem 52 and a cellular telephone 61 to provide data display and communications capabilities within the chase vehicle 22. It should also be noted that the electronics involved with the ultrasonic testing system have been used in the industry for several years and are well within the skill of one of ordinary skill in this art. Further, programming of the computers may be accomplished by one of ordinary skill in the computer programming art given the parameters defined by the present method.

Returning now to FIG. 1, and to the equipment within the test vehicle 10, the digital computer 34 is in communication with a storage device 40 over communication lines 60. Further, the analog computer 42 is in communication with a data storage device 46 through communication line 62. The digital computer 34 and the analog computer 42 exchange data over data lines 64, 66. The analog computer 42 is in communication with the ultrasonic processing apparatus 72 through data line 78 while the digital computer 34 is in communication with the ultrasonic testing apparatus 72 through data communication line 76. A radio frequency modem 48 including a data multiplexer and receiver/transmitter is provided within the test vehicle 10 in communication with the digital computer 34 through data communication line 68. An antenna 50 is provided for transmission and reception of electronic signals. The test vehicle 22 includes a similar radio frequency modem 52 including a data multiplexer and receiver/transmitter. The second radio modem 52 is in communication with the second computer 56 through data lines 80, 82 and is connected using a typical RS232 connection. An antenna 54 is provided and is operatively associated with the second radio modem 52 for transmission and reception of data signals.

Figure 4:
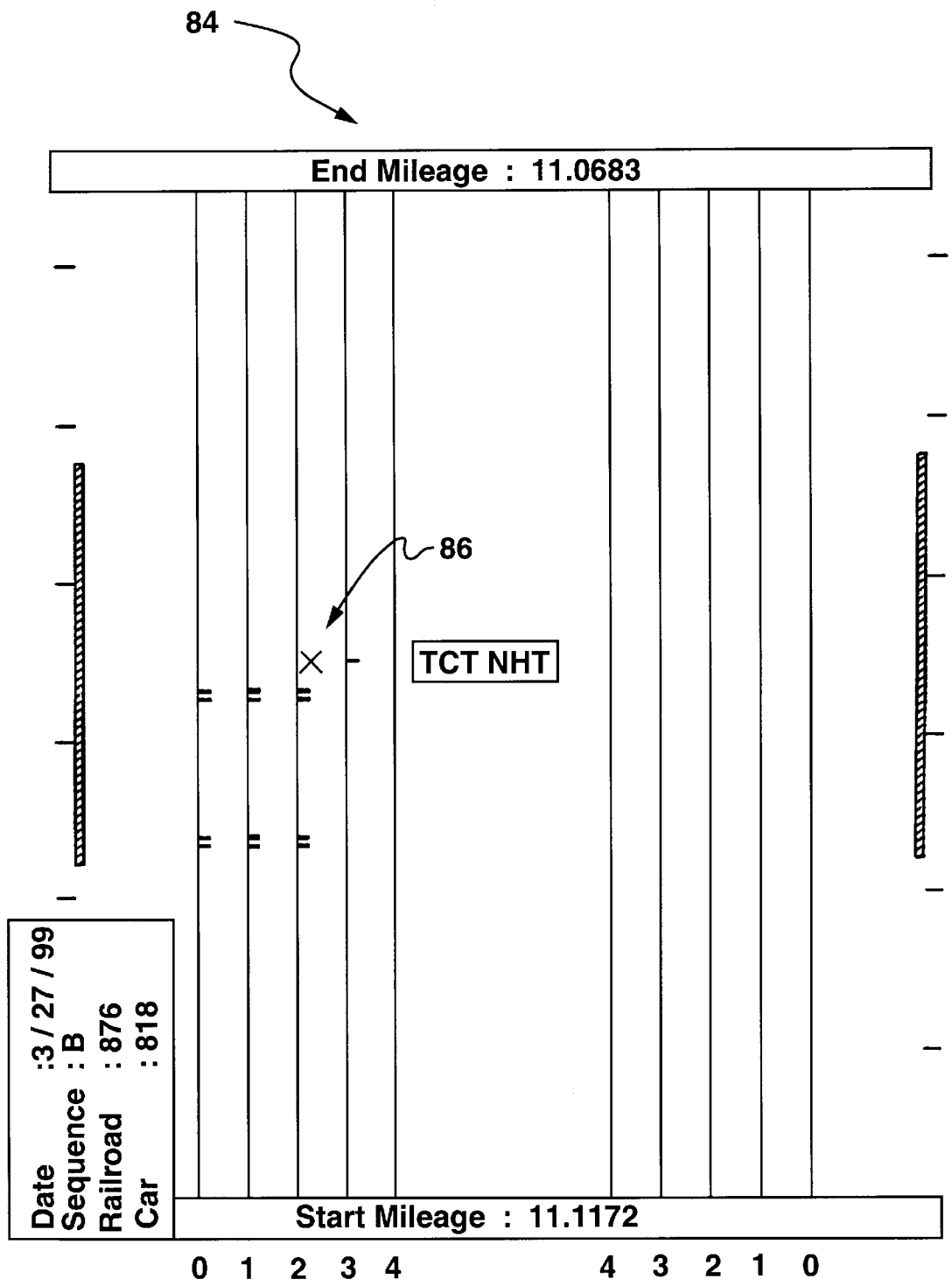
FIG. 4 is a representation of the digital display according to the preferred embodiment of the present invention.

According to the method of the present invention and according to the preferred operation of the apparatus of the present invention, the test vehicle FIG. 3 is caused to move along the rails 92 in advance of the chase vehicle 22 as illustrated in FIG. 3. During movement along the rails 92, ultrasonic testing is conducted using the rail testing apparatus 72 with the transducer 74 emitting and receiving signals within the rails. The data is processed within the ultrasonic processor 122 and delivered to the digital and analog displays. As seen in FIG. 4, the digital display is illustrated generally at 84 and includes the location of an anomaly 86. Different signals are presented which are directed to the 0° signal, the 37° signal, the 70° signal, an alarm signal, and a triple web signal. The data displayed is the data that has been processed using logic within the ultrasonic test processor 122. The position down the screen indicates the defect location and the vertical lines represent the different channels of ultrasonic information.

Figure 5:
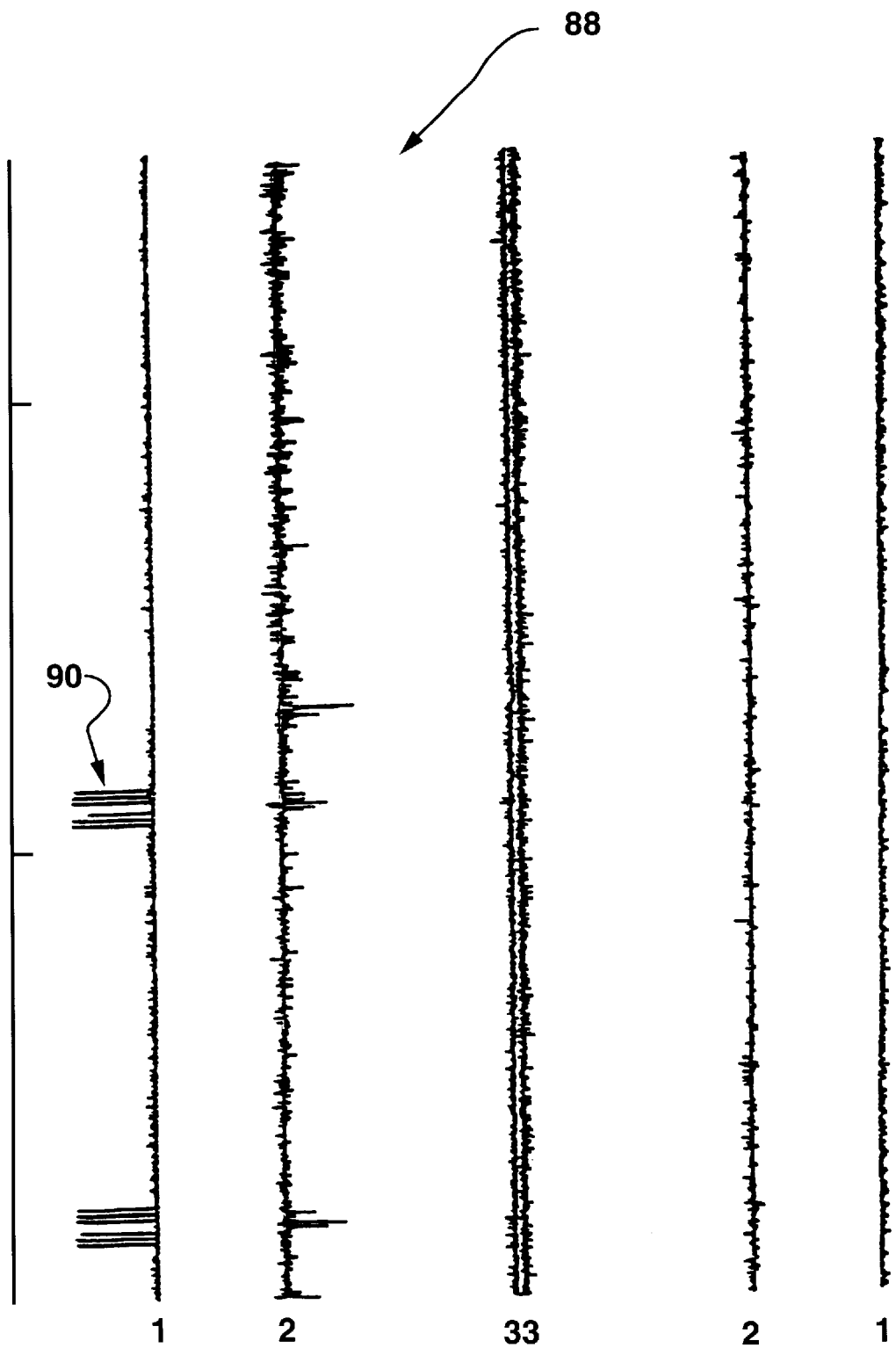
FIG. 5 is a representation of the analog display according to the preferred embodiment of the present invention.

With reference to FIG. 5, the analog information is displayed and illustrated generally at 88. Once again, the vertical distance represents the defect location along the track. An anomaly is illustrated in 90. The two displays are viewed by the operator and any combination of signals at a particular location that could possibly be a defect are selected. The selection is made using the light pen 38 which is touched to the screen. When this is done, the digital computer 34, which is linked to the analog computer 42, captures a "snapshot" of analog data centered on the location of the light pen selection. The length of the "snapshot" is one screen of data which equates to approximately 80–120 feet depending on the vehicle's speed and distance setting. The analog "snapshot" is stored on the digital computer with the digital data.

When the selection is made on the digital screen 36, the operator is asked to pre-classify the suspect selection. This is done by selecting the appropriate defect classification with the light pen 38 on a menu bar (not shown) that appears at the bottom of the digital screen 36. A confirmation is then requested. If the confirmation is selected with the light pen 38, the data, including digital, analog and positional data, is transmitted to the chase vehicle 22. If the selection is not confirmed, the system will timeout and transmit the data to the chase vehicle 22. If the selection is retracted, no data is transmitted. Several rail lengths of digital data is transmitted. Then paint is applied to the rails 92 for certain predetermined combinations of data. Further, the test vehicle 10 applies a paint mark on the rail head every 0.1 mile down the track to aid the defect location effort when the chase vehicle 22 follows up. Both vehicles are equipped with encoders 20, 30 which are manually synchronized at the start of each day and at each milepost location on the track. The 0.1 mile paint mark acts as a backup.

The radio modems 48, 52 have their own FCC licensed frequency and thus do not interfere with any other radio transmission. The transmission distance achieved is between 5 and 10 miles depending on the terrain. If, for whatever reason, the radio modems 48, 52 lose contact, both vehicles 10, 22 are made aware of the situation by annotations on their respective display devices 36, 58. The test vehicle 10 operator can select a "re-send" button which instructs the radio modem 48 to resend all pending information. The system employs a handshaking protocol such that the pending information will include everything that the test vehicle 10 system has not had an acknowledgment of as being successfully received by the chase vehicle 22. Chase vehicle 22 display 58 as illustrated in FIG. 6 shows a continuously updated display of the test vehicle location. If this stops, the radio link has presumed to have been broken. The test vehicle 10 is made aware of the number of packets of data to be sent to the chase vehicle 22. If this keeps increasing, then, once again, the radio link has likely been broken. If the radio link cannot be reestablished, the test vehicle 10 can revert to the standard "stop and confirm" test mode which eliminates the use of the chase vehicle 22. This does not require any action on the part of the operator and it can continue as long as necessary, i.e., until the radio link is reformed.

The data sent to the chase vehicle 22 is displayed on the laptop computer 56 acting as the second computer of the present invention. The data sent includes the digital and positional data and, if selected, the analog data. The laptop display is a list of the "suspects" or suspected rail defects sent to the chase vehicle as illustrated in 56. The suspects are listed at 94 in FIG. 6. Selection of one of the suspects will bring up the digital data associated with that suspect and, if it is available, the analog data can be viewed from there as well. The suspect list 94 also provides rail segment information, the status/result 98, the recording operator 100, the examining operator 102, and mileage location 104. Once the chase vehicle has located the spot on the track, the requisite confirmatory action is completed either by a ground examination or a hand test. The results of the ground examination or hand test are entered into the laptop computer 56 for that location. If the test vehicles had to stop in the "stop and confirm" mode, the complete details of the inspection are transmitted to the chase vehicle 22 such that the location is not inspected twice. If the operator on the chase vehicle 22 considers that he has insufficient data, he can request more digital data from the test vehicle 10 by using a single keystroke on the laptop or second computer 56. This action does not affect the operation of the test vehicle 10. The results of all confirmatory actions on the chase vehicle 22 are transmitted to the test vehicle 10 such that both vehicles have a complete record of the inspection.

By the above, the chase vehicle 22 personnel obtain complete data with regard to the rail conditions such that proper actions may be taken with regard to rail inspections. Further, complete records are compiled in both the test vehicle 10 and the chase vehicle 22 providing a redundancy-based data safeguard. The present invention will provide greater speed and flexibility associated with rail inspections.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A method for testing rails for structural defects, the rails being associated with a railroad track, ground supported and extending in a generally parallel manner along a roadbed, said method comprising the steps of:

providing a first rail traveling vehicle for movement along a segment of rails for testing, said first rail traveling vehicle being equipped with a rail testing apparatus for the production of data indicative of rail conditions and a first computer system in data exchanging communication with said rail testing apparatus, said first computer system having a display arrangement for displaying digital data and analog data associated with rails tested by said rail testing apparatus, and a control interface for computer control by an operator;

providing a second rail traveling vehicle for disposition behind said first rail traveling vehicle along said segment of rails for testing, said second rail traveling vehicle having a second computer disposed therein for display of data associated with rails tested by said rail testing apparatus;

providing a first modem assembly operatively associated with said first computer system and a second modem assembly operatively associated with said second computer, said first modem assembly being in data exchanging communication with said second modem assembly for data exchange between said first computer and said second computer;

moving said first rail traveling vehicle and said second rail traveling vehicle along rails to be tested, said first rail traveling vehicle moving in advance of said second rail traveling vehicle;

testing predetermined rail segments using said rail testing apparatus, with said rail testing apparatus communicating rail test data associated with the structural condition of a tested rail segment to said first computer;

displaying said rail test data on a computer screen wherein said rail test data may include data indicative of a structural defect in said predetermined rail segment at a defect location along said rail;

assessing said rail test data to determine if said rail test data is indicative of a possible structural defect in said predetermined rail segment at a defect location;

selecting, upon detection of a possible structural defect, data indicative of the possible structural defect at the defect location, thereby creating a data snapshot of structural conditions along the segment of rails having the possible defect therein;

communicating said data indicative of the possible structural defect at the defect location from said first computer system to said second computer using said first modem assembly and said second modem assembly;

displaying said data indicative of the possible structural defect at the defect location using said second computer; and assessing said data indicative of the possible structural defect at the defect location to locate the defect location and the possible structural defect in order to carry out a manual defect confirmation test and, if necessary, to initiate repair procedures.

2. A method for testing rails for structural defects according to claim 1 wherein said step of providing a first computer system includes providing a first digital computer and further includes providing a first analog computer in data exchanging communication with said first digital computer, with said first digital computer being for processing digital rail test data and said first analog computer being for processing analog rail test data.

3. A method for testing rails for structural defects according to claim 2 wherein said step of providing a first computer system includes providing a first display arrangement associated with said first digital computer for displaying digital rail test data and a second display arrangement associated with said first analog computer for displaying analog rail test data and said step of assessing said rail test data includes viewing and assessing digital rail test data in conjunction with corresponding analog rail test data to determine if said rail test data is indicative of a possible structural defect in said predetermined rail segment at a defect location.

4. A method for testing rails for structural defects according to claim 3 wherein said step of communicating said data indicative of the possible structural defect to said second computer includes communicating digital rail test data and possible defect location data to said second computer.

5. A method for testing rails for structural defects according to claim 4 wherein said step of communicating said data indicative of the possible structural defect to said second computer includes communicating analog rail test data to said second computer.

6. A method for testing rails for structural defects according to claim 2 wherein said step of selecting data indicative of a possible structural defect, thereby creating a digital snapshot of structural conditions includes said first digital computer communicating with said first analog computer to capture analog data selected, said analog data selected being indicative of a defect and a location of said defect.

7. A method for testing rails for structural defects according to claim 6 wherein said step of providing said first computer system includes providing a light pen used to select data by touching said light pen to a display and said step of selecting data indicative of a possible structural defect, thereby creating a digital snapshot of structural conditions includes using said light pen to select data by touching said light pen to said digital display at a position on said display corresponding to a possible defect location.

8. A method for testing rails for structural defects according to claim 6 wherein said step of selecting data indicative of a possible structural defect, thereby creating a digital snapshot of structural conditions includes creating a snapshot of data corresponding to a rail segment having a linear dimension in the range of approximately 80–240 feet.

9. A method for testing rails for structural defects according to claim 1 wherein said step of selecting, upon detection of a possible structural defect, data indicative of the possible structural defect at the defect location includes the step of selecting a defect classification from a list of predetermined defect classifications stored in said first computer.

10. A method for testing rails for structural defects according to claim 9 wherein said step of selecting, upon detection of a possible structural defect, data indicative of the possible structural defect at the defect location includes the step of confirming the selection of a defect prior to communicating said rail test data to said second computer, and if said confirmation step is omitted, test data conforming to a predetermined rail length is transmitted.

11. A method for testing rails for structural defects according to claim 9 and further comprising the step of applying paint to the rails in a predetermined manner based on particular combinations of test data.

12. A method for testing rails for structural defects according to claim 1 wherein said step of providing a first modem assembly operatively associated with said first computer system and a second modem assembly operatively associated with said second computer, said first modem assembly being in data exchanging communication with said second modem assembly for data exchange between said first computer system and said second computer includes the step of providing a first radio transmitter and receiver operatively associated with said first computer system and a second radio transmitter and receiver operatively associated with said second computer for maintaining radio communication between said first computer and said second computer for wireless data exchange therebetween.

13. A method for testing rails for structural defects according to claim 12 wherein said step of providing radio transmitters and receivers includes providing means for determining when communications between said first computer system and said second computer have been terminated operatively associated with said first computer and said second computer, and upon discovery of such termination of communications, the method further includes the step of alerting operators to such termination and the step of resending all data that has not been acknowledged by said second computer.

14. A method for testing rails for structural defects according to claim 13 wherein said step of providing a second display includes providing said second display with information regarding a location of said first rail traveling vehicle along said rails, and upon loss of said location information, said method includes the step of determining that said communication has terminated.

15. A method for testing rails for structural defects according to claim 1 and further comprising the step of entering results associated with said manual rail test into said second computer and communicating said result data to said first computer.

16. An apparatus for testing rails for structural defects, the rails being associated with a railroad track, ground supported and extending in a generally parallel manner along a roadbed, said apparatus comprising:

a first rail traveling vehicle for movement along a segment of rails for testing, said first rail traveling vehicle having a rail testing apparatus for the production of data indicative of rail conditions mounted thereto;

a first computer system mounted within said first rail traveling vehicle in data exchanging communication with said rail testing apparatus, said first computer having a display arrangement for displaying digital data and analog data associated with rails tested by said rail testing apparatus, and a control interface for computer control by an operator;

a second rail traveling vehicle for disposition behind said first rail traveling vehicle along said segment of rails for testing;

a second computer disposed in said second rail traveling vehicle for display of data associated with rails tested by said rail testing apparatus;

a first modem assembly operatively associated with said first computer and mounted within said first rail traveling vehicle;

a second modem assembly operatively associated with said second computer and disposed within said second rail traveling vehicle, said first modem assembly being in data exchanging communication with said second modem assembly for data exchange between said first computer and said second computer to communicate data indicative of a possible structural defect at a defect location to said second computer using said first modem assembly and said second modem assembly; and means for displaying said data indicative of the possible structural defect at the defect location operatively associated with said second computer for assessment of said data indicative of the possible structural defect at the defect location to locate the defect location and the possible structural defect in order to carry out a manual defect confirmation test and, if necessary, to initiate repair procedures.

17. An apparatus for testing rails for structural defects according to claim 16 wherein said first computer system includes a first digital computer and further includes a first analog computer in data exchanging communication with said first digital computer, with said first digital computer including means for processing digital rail test data and said first analog computer including means for processing analog rail test data.

18. An apparatus for testing rails for structural defects according to claim 17 wherein said first computer system includes a first display apparatus operatively associated with said first digital computer for displaying digital rail test data and a second display apparatus operatively associated with said first analog computer for displaying analog rail test data for assessment of said rail test data by action of an operator in viewing and assessing digital rail test data in conjunction with corresponding analog rail test data to determine if said rail test data is indicative of a possible structural defect in said predetermined rail segment at a defect location.

19. An apparatus for testing rails for structural defects according to claim 18 wherein said first computer system includes means for communicating said data indicative of the possible structural defect including analog rail test data to said second computer.

20. An apparatus for testing rails for structural defects according to claim 16 wherein said first digital computer includes means for communicating with said first analog computer to capture analog data selected by an operator, said analog data being indicative of a defect and a location of said defect.

21. An apparatus for testing rails for structural defects according to claim 20 wherein said control interface includes a light pen for use by an operator to select data by touching said light pen to a position on said display corresponding to a possible defect location, said data being indicative of a possible structural defect, to thereby create a digital snapshot of structural conditions.

22. An apparatus for testing rails for structural defects according to claim 16 and wherein said first rail traveling vehicle includes means for applying paint to the rails in a predetermined manner based on particular combinations of test data.

23. An apparatus for testing rails for structural defects according to claim 16 and further comprising a first radio transmitter and receiver operatively associated with said first modem assembly and a second radio transmitter and receiver operatively associated with said second modem assembly, for maintaining radio communication between said first computer and said second computer for wireless data exchange therebetween.

24. An apparatus for testing rails for structural defects according to claim 23 and further comprising means for determining when communications between said first rail traveling vehicle and said second rail traveling vehicle have been terminated, and means for, upon discovery of such termination of communications, alerting operators to such termination, operatively associated with said transmitters and receivers.

25. An apparatus for testing rails for structural defects, the rails being associated with a railroad track, ground supported and extending in a generally parallel manner along a roadbed, said apparatus comprising:

a first rail traveling vehicle for movement along a segment of rails for testing, said first rail traveling vehicle having a rail testing apparatus for the production of data indicative of rail conditions mounted thereto;

a first computer system mounted within said first rail traveling vehicle in data exchanging communication with said rail testing apparatus, said first computer including a first digital computer and a first analog computer in data exchanging communication with said first digital computer, with said first digital computer including means for processing digital rail test data and said first analog computer including means for processing analog rail test data, and further including a display arrangement for displaying digital data and analog data associated with rails tested by said rail testing apparatus, said display arrangement including a first display apparatus operatively associated with said first digital computer for displaying digital rail test data and a second display apparatus operatively associated with said first analog computer for displaying analog rail test data for assessment of said rail test data by action of an operator in viewing and assessing digital rail test data in conjunction with corresponding analog rail test data to determine if said rail test data is indicative of a possible structural defect in said predetermined rail segment at a defect location and a control interface for operational computer control by an operator, said control interface including a light pen for use by an operator to select data by touching said light pen to a position on said display corresponding to a possible defect location, said data being indicative of a possible structural defect, to thereby create a digital snapshot of structural conditions;

a second rail traveling vehicle for disposition behind said first rail traveling vehicle along said segment of rails for testing;

a second computer disposed in said second rail traveling vehicle for display of data associated with rails tested by said rail testing apparatus;

a first modem assembly operatively associated with said first computer and mounted within said first rail traveling vehicle;

a second modem assembly operatively associated with said second computer and disposed within said second rail traveling vehicle, said first modem assembly being in data exchanging communication with said second modem assembly for data exchange between said first computer and said second computer to communicate data indicative of a possible structural defect at a defect location to said second computer using said first modem assembly and said second modem assembly;

a radio transmitter and receiver operatively associated with said first modem assembly and a radio transmitter and receiver operatively associated with said second modem assembly, for maintaining radio communication between said first computer and said second computer for wireless data exchange therebetween; and means for displaying said data indicative of the possible structural defect at the defect location operatively associated with said second computer for assessment of said data indicative of the possible structural defect at the defect location to locate the defect location and the possible structural defect in order to carry out a manual defect confirmation test and, if necessary, to initiate repair procedures.

26. An apparatus for testing rails for structural defects according to claim 25 wherein said first computer system includes means for communicating said data indicative of the possible structural defect to said second computer including analog rail test data to said second computer.

27. An apparatus for testing rails for structural defects according to claim 25 wherein said first digital computer includes means for communicating with said first analog computer to capture analog data selected by an operator, said analog data being indicative of a defect and a location of said defect.

28. An apparatus for testing rails for structural defects according to claim 25 and wherein said first rail traveling vehicle includes means for applying paint to the rails in a predetermined manner based on particular combinations of test data.

29. An apparatus for testing rails for structural defects according to claim 25 and further comprising means for determining when communications therebetween have been terminated, and means for, upon discovery of such termination of communications, alerting operators to such termination, operatively associated with said transmitters and receivers.

* * * * *